United States Patent [19]

Kim

[11] Patent Number: 4,906,475

[45] Date of Patent: Mar. 6, 1990

[54] ESTRADIOL TRANSDERMAL DELIVERY SYSTEM

[75] Inventor: Benjamin K. Kim, Toms River, N.J.

[73] Assignee: Paco Pharmaceutical Services, Lakewood, N.J.

[21] Appl. No.: 156,266

[22] Filed: Feb. 16, 1988

[51] Int. Cl.[4] ........................................... A61F 13/00
[52] U.S. Cl. .................................. 424/449; 424/448; 424/487
[58] Field of Search ............................... 424/448, 449

[56] References Cited

U.S. PATENT DOCUMENTS

| | | | |
|---|---|---|---|
| 3,249,109 | 11/1963 | Maeth et al. ........................ | 128/268 |
| 3,426,754 | 2/1969 | Bierenbaum et al. ............... | 128/156 |
| 3,464,413 | 9/1969 | Goldfarb et al. ................... | 128/268 |
| 3,472,931 | 10/1969 | Stoughton . | |
| 3,527,864 | 9/1970 | MacMillan et al. ................ | 424/177 |
| 3,598,122 | 8/1971 | Zaffaroni ............................ | 128/268 |
| 3,598,123 | 8/1971 | Zaffaroni ............................ | 128/268 |
| 3,632,740 | 1/1971 | Robinson et al. ................... | 424/28 |
| 3,641,237 | 2/1972 | Gould et al. ........................ | 424/16 |
| 3,699,963 | 10/1972 | Zaffaroni ............................ | 128/268 |
| 3,731,683 | 5/1973 | Zaffaroni ............................ | 128/268 |
| 3,737,521 | 6/1973 | Born ................................... | 424/22 |
| 3,742,951 | 7/1973 | Zaffaroni ............................ | 128/268 |
| 3,767,786 | 10/1973 | MacMillan .......................... | 424/65 |
| 3,783,869 | 1/1974 | Schnipper ........................... | 128/261 |
| 3,797,494 | 3/1974 | Zaffaroni ............................ | 128/268 |
| 3,849,238 | 11/1974 | Gould et al. ........................ | 161/159 |
| 3,867,520 | 2/1975 | Mori et al. .......................... | 424/36 |
| 3,892,842 | 7/1975 | Zaffaroni ............................ | 424/22 |
| 3,896,238 | 7/1975 | Smith .................................. | 424/358 |
| 3,903,256 | 9/1975 | MacMillan et al. ................. | 424/59 |
| 3,903,880 | 9/1975 | Higuchi et al. ..................... | 128/130 |
| 3,921,636 | 11/1975 | Zaffaroni ............................ | 128/260 |
| 3,926,188 | 12/1975 | Baker et al. ........................ | 128/260 |
| 3,932,653 | 1/1976 | Stoughton . | |
| 3,946,106 | 3/1976 | Chien et al. ........................ | 424/15 |
| 3,948,254 | 4/1976 | Zaffaroni ............................ | 128/127 |
| 3,952,099 | 8/1976 | Smith .................................. | 424/227 |
| 3,964,482 | 6/1976 | Gerstel et al. ...................... | 128/260 |
| 3,969,516 | 7/1976 | Stoughton . | |
| 3,972,995 | 8/1976 | Tsuk et al. .......................... | 424/28 |
| 3,992,518 | 10/1976 | Chien et al. ........................ | 424/22 |

(List continued on next page.)

FOREIGN PATENT DOCUMENTS

| | | | |
|---|---|---|---|
| 0764422 | 8/1971 | Belgium .............................. | 424/28 |
| 0930668 | 7/1973 | Canada ................................ | 128/268 |
| 144486 | 6/1985 | European Pat. Off. . | |
| 3333240 | 3/1985 | Fed. Rep. of Germany . | |
| 2224126 | 10/1974 | France ................................. | 424/80 |
| 2224140 | 10/1974 | France ................................. | 424/80 |
| 2437830 | 4/1980 | France . | |
| 0537493 | 3/1978 | Japan . | |
| 139011 | 8/1982 | Japan . | |
| 058913 | 6/1983 | Japan . | |
| 87/03490 | 6/1987 | PCT Int'l Appl. . | |
| 1001949 | 1/1965 | United Kingdom . | |
| 1108837 | 4/1968 | United Kingdom . | |
| 2021950 | 12/1979 | United Kingdom . | |
| 2158355 | 11/1985 | United Kingdom . | |

OTHER PUBLICATIONS

Cooper, E. R., "Increased Skin Permeability for Lipophilic Molecules", J. Pharm. Sci., Aug. 1984, vol. 73, No. 8, pp. 1153–1156.

F. S. Kilmer MacMillan, et al., "The Antiperspirant Action of Topically Applied Anticholinergics", The Journal of Investigative Dermatology, vol. 43, pp. 363–377, 1964.

(List continued on next page.)

Primary Examiner—Ellis P. Robinson
Assistant Examiner—Leon R. Horne
Attorney, Agent, or Firm—Seidel, Gonda, Lavorgna & Monaco

[57] ABSTRACT

The present invention is directed to a transdermal delivery system for an active substance. The active substance is estrogen or its derivatives and preferably is 17-beta-estradiol. The system comprises an impermeable backing layer and a matrix affixed thereto. The matrix comprises, on a weight percentage basis, from about 60 to about 95% of an adhesive polymer, from about 5 to about 20% of a solvent, from about 0.2 to about 4% of a skin penetration enhancer, and from about 0.5 to about 5% of the active substance. The system is free of any discrete permeable, polymeric, diffusion-controlling membrane.

8 Claims, 3 Drawing Sheets

U.S. PATENT DOCUMENTS

| | | | |
|---|---|---|---|
| 3,993,072 | 10/1976 | Zaffaroni | 128/260 |
| 3,993,073 | 11/1976 | Zaffaroni | 128/260 |
| 3,996,934 | 12/1976 | Zaffaroni | 128/268 |
| 4,012,497 | 3/1977 | Schopflin | 424/22 |
| 4,016,251 | 4/1977 | Higuchi et al. | 424/15 |
| 4,018,889 | 4/1977 | Armstrong. | |
| 4,031,894 | 6/1977 | Urquhart | 128/268 |
| 4,039,664 | 8/1977 | Stoughton et al. | |
| 4,046,886 | 9/1977 | Smith | 424/827 |
| 4,053,580 | 11/1977 | Chandraskaran et al. | 128/260 |
| 4,058,122 | 11/1977 | Theeuwes | 128/260 |
| 4,060,084 | 11/1977 | Chandrasekaran et al. | 128/260 |
| 4,069,307 | 1/1978 | Higuchi et al. | 424/22 |
| 4,077,407 | 3/1978 | Theeuwes et al. | 128/260 |
| 4,096,239 | 6/1978 | Katz et al. | 128/260 |
| 4,127,127 | 11/1978 | Wong et al. | 128/260 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,162,243 | 7/1979 | Lee et al. | 260/37 SB |
| 4,177,256 | 12/1979 | Michaels et al. | 424/22 |
| 4,180,646 | 12/1979 | Choi et al. | 528/153 |
| 4,201,211 | 5/1980 | Chandraskaran et al. | 128/268 |
| 4,230,105 | 10/1980 | Harwood | 128/156 |
| 4,237,888 | 12/1980 | Roseman et al. | 128/270 |
| 4,262,003 | 4/1981 | Urquhart et al. | 424/267 |
| 4,286,592 | 9/1981 | Chandraskaran et al. | 128/260 |
| 4,289,749 | 9/1981 | Keith et al. | 424/28 |
| 4,291,014 | 9/1981 | Keith et al. | 424/28 |
| 4,291,015 | 9/1981 | Keith et al. | 424/28 |
| 4,292,301 | 9/1981 | Keith et al. | 424/28 |
| 4,292,302 | 9/1981 | Keith et al. | 424/28 |
| 4,292,303 | 9/1981 | Keith et al. | 424/28 |
| 4,294,820 | 10/1981 | Keith et al. | 424/28 |
| 4,297,995 | 11/1981 | Golub | 128/158 |
| 4,299,826 | 11/1981 | Luedders | 424/181 |
| 4,314,557 | 2/1982 | Chandrasekaran | 128/260 |
| 4,321,252 | 3/1982 | Keith et al. | 424/28 |
| 4,335,115 | 6/1982 | Thompson et al. | 424/181 |
| 4,336,243 | 5/1982 | Sanvordekor | 424/28 |
| 4,343,798 | 8/1982 | Fawzi | 424/240 |
| 4,379,454 | 4/1983 | Campbell et al. | 604/897 |
| 4,390,520 | 6/1983 | Nagai et al. | 424/28 |
| 4,405,616 | 9/1983 | Rajadhyaksha | 424/244 |
| 4,409,206 | 8/1983 | Stricker | 424/81 |
| 4,420,470 | 12/1983 | Otsuka et al. | 424/28 |
| 4,428,925 | 12/1984 | Keith | 424/19 |
| 4,435,180 | 3/1984 | Leeper | 604/896 |
| 4,436,741 | 3/1984 | Urquhart et al. | 424/267 |
| 4,438,139 | 3/1984 | Keith et al. | 424/28 |
| 4,460,368 | 7/1984 | Allison et al. | 604/896 |
| 4,460,371 | 7/1984 | Abber | 604/897 |
| 4,460,372 | 7/1984 | Campbell et al. | 604/897 |
| 4,466,953 | 8/1984 | Keith et al. | 424/28 |
| 4,470,962 | 9/1984 | Keith et al. | 424/28 |
| 4,482,534 | 11/1984 | Blank | 424/28 |
| 4,483,846 | 11/1984 | Koide et al. | 424/19 |
| 4,485,087 | 11/1984 | Otsuka et al. | 424/28 |
| 4,486,193 | 12/1984 | Shaw et al. | 604/897 |
| 4,490,322 | 12/1984 | Zierenberg | 264/205 |
| 4,492,685 | 1/1985 | Keith et al. | 424/28 |
| 4,505,891 | 3/1985 | Ito | 424/28 |
| 4,533,540 | 8/1985 | Blank | 424/28 |
| 4,542,013 | 9/1985 | Keith et al. | 424/28 |
| 4,552,751 | 11/1985 | Inaba et al. | 424/19 |
| 4,558,580 | 5/1986 | Gale et al. | 424/21 |
| 4,559,222 | 12/1986 | Enscore et al. | 424/28 |
| 4,564,010 | 1/1986 | Coughlan et al. | 128/156 |
| 4,564,364 | 1/1986 | Zaffaroni et al. | 604/897 |
| 4,568,343 | 2/1986 | Leeper et al. | 604/896 |
| 4,573,995 | 3/1986 | Chen et al. | 604/896 |
| 4,579,731 | 4/1986 | Fox, Jr. et al. | 424/28 |
| 4,585,452 | 4/1986 | Sablotsky | 604/896 |
| 4,585,797 | 4/1986 | Cioca | 514/773 |
| 4,591,501 | 5/1986 | Cioca | 424/28 |
| 4,592,753 | 6/1986 | Panoz | 604/897 |
| 4,594,240 | 6/1986 | Kawata et al. | 424/28 |
| 4,595,391 | 6/1986 | Abplanalp | 604/308 |
| 4,597,960 | 7/1986 | Cohen | 424/28 |
| 4,601,893 | 7/1986 | Cardinal | 424/15 |
| 4,608,249 | 8/1986 | Otsuka et al. | 424/28 |
| 4,614,787 | 9/1986 | Szycher et al. | 528/75 |
| 4,615,697 | 10/1986 | Robinson | 604/890 |
| 4,615,699 | 10/1986 | Gale et al. | 604/897 |
| 4,623,346 | 11/1986 | Von Bittera et al. | 604/896 |
| 4,624,665 | 11/1986 | Nuwayser | 604/307 |
| 4,627,852 | 12/1986 | von Bittera et al. | 604/897 |
| 4,638,043 | 1/1987 | Szycher et al. | 528/75 |
| 4,655,767 | 4/1987 | Woodard et al. | 604/896 |
| 4,655,768 | 4/1987 | Marecki et al. | 604/897 |
| 4,661,104 | 4/1987 | von Bittera et al. | 604/896 |
| 4,661,105 | 4/1987 | Gale et al. | 604/897 |
| 4,666,441 | 5/1987 | Andriola et al. | 604/897 |
| 4,668,232 | 5/1987 | Cordes et al. | 604/897 |
| 4,668,506 | 5/1987 | Bawa | 424/429 |
| 4,675,009 | 6/1987 | Hymes et al. | 604/304 |
| 4,685,911 | 8/1987 | Konno et al. | 604/897 |
| 4,687,481 | 8/1987 | Nuwayser | 604/897 |

(List continued on next page.)

U.S. PATENT DOCUMENTS

| | | | |
|---|---|---|---|
| 4,690,683 | 9/1987 | Chiba | 424/448 |
| 4,692,462 | 9/1987 | Banerjee | 514/449 |
| 4,693,776 | 9/1987 | Krampe et al. | 156/327 |
| 4,695,464 | 9/1987 | Alderman | 424/449 |
| 4,695,465 | 9/1987 | Kigasawa et al. | 424/449 |
| 4,696,821 | 9/1987 | Belsole | 424/448 |
| 4,698,062 | 10/1987 | Gale et al. | 604/896 |
| 4,699,146 | 10/1987 | Sieverding | 128/640 |
| 4,699,777 | 10/1987 | Zupon et al. | 424/28 |
| 4,704,282 | 11/1987 | Campbell et al. | 424/449 |
| 4,710,191 | 12/1987 | Kwiatek et al. | 604/897 |
| 4,710,383 | 12/1987 | Dick | 424/449 |
| 4,713,243 | 12/1987 | Schiraldi et al. | 424/151 |
| 4,725,439 | 2/1988 | Campbell et al. | 424/449 |
| 4,732,808 | 3/1988 | Krampe et al. | 428/355 |
| 4,732,915 | 3/1988 | Ayer et al. | 514/567 |
| 4,738,670 | 4/1988 | von Bittera | 604/306 |
| 4,740,374 | 4/1988 | Nakano et al. | 424/448 |
| 4,743,249 | 5/1988 | Loveland | 424/447 |
| 4,746,509 | 5/1988 | Haggiage et al. | 424/449 |
| 4,746,515 | 5/1988 | Cheng et al. | 424/449 |
| 4,747,845 | 5/1988 | Korol | 604/368 |
| 4,749,574 | 6/1988 | Ueda et al. | 424/448 |
| 4,751,087 | 6/1988 | Wick | 424/449 |
| 4,764,379 | 8/1988 | Sanders et al. | 424/449 |
| 4,769,028 | 9/1988 | Hoffmann et al. | 424/443 |
| 4,778,678 | 10/1988 | Guse et al. | 424/487 |
| 4,778,786 | 10/1988 | Reever et al. | 514/54 |
| 4,781,924 | 11/1988 | Lee et al. | 424/449 |
| 4,784,857 | 11/1988 | Berry et al. | 424/449 |
| 4,788,062 | 11/1988 | Gale et al. | 424/449 |

OTHER PUBLICATIONS

A. S. Michaels et al., Drug Permeation Through Human Skin: Theory and in vitro Experimental Measurement, *American Institute of Chemical Engineers Journal*, vol. 21, No. 5, pp. 985–996, 1975.

Dow Corning, New Product Information Brochure, Silastic ® Q7-4840 A/B Medical Grode Liquid Silicone Rubber (LSR) 1981.

Valia, et al. "Transdermal Controlled Administration of Estradiol Derviates and Structure-Kinetic Relationships", Dissertaton Abstracts Intn'l vol. 46, No. 2, 8/85.

Chein, et al., "Long Term Permeation Kinetics of Estradiol", Drug Development and Industrial Pharmacy, vol. 11, Nos. 6 & 7, pp. 1195–1212, 1985.

Guy et al., "Interpretation and Prediciton of the Kinetics of Transdermal Drug Delivery: oestradiol, hyoscine and timolol", Intn'l J. of Pharmaaceutics, vol. 32, pp. 159–163 (1986).

Acharya, et al., "Observations on 17-B-Hydroxysteriod Dehydrogenase in the Broad Patch of House Sparrow", Current Sci., vol. 53, No, 3, pp. 160–162, 2/1984.

Judd, "Efficacy of Transdermal Estradiol", Am. J. Obstet Gynecol, May 1987.

Jones, et al., "Incubation Patch of the Chicken", Gen. and Comp Endocr. vol. 15, pp. 398–403, 1970.

Hutchinson, et al., "The Effects of Estrogen Progesterone and Prolactin on Brood Patch Formation in Ovariectomized Canaries", J. Endocr., vol. 39, pp. 379–385 (1967).

Hohn, "Failure to Induce Incubation Behavior . . . " Gen. and Comp. Endocr., vol. 44, pp. 396–399 (1981).

Padwick et al., "Efficacy, Acceptability, and Metabolic Effects of Transdermal Estradiol . . . ", Am J. Obstet Gyncol., p. 1085 et seq. 8/1985.

Chetkowski, et al., "Biological Effects of Transdermal Estradiol", New Eng. J. of Med. vol. 314, No. 25, p. 1615 et seq., Jun. 1986.

Selby, et al., "The Effect of Transermal Oestrogen Bone . . . ", Clin. Endocr., vol. 25, pp. 543–547, 1986.

Tojo, et al., "Bioconversion of Estradiol Esters in Hairless Mouse Skin in Vitro", Chemical Eng. J., vol. 33, B63–B67, 1986.

Baker, et al., "Patients in Transermal Drug Delivery", Drug Delivery Systems, pp. 26–31 (1987).

CTFA-Cosmetic Ingredient Dictionary, 1st ed., The Cosmetic, Toiletry, and Fragrance Assocation, Inc., Washington, D.C. 1973, pp. 126–127.

Idson, B., "Perculaneous Absorption", Journal of Pharm. Sci., Jun. 1975, pp. 901–924.

Higuchi, T., "Rate of Release of Medicaments from Ointment Bases Containing Drugs in Suspension," J. of Pharm. Sci., Oct. 1961, pp. 874–875.

"Cases Where the Rate Controlling Step is in the Applied Phase", J. of Soc. of Cosmetic Chemists, pp. 94–97.

Haleblian, J. et al., "Steroid Release from Silicone Elastomer Containing Excess Drug in Suspension", J. Pharm. Sci., Apr. 1971, pp. 541–545.

Bottari, F. et al., "Influence of Drug Concentration on In Vitro Release of Salicyclic Acid from Ointment Bases", J. Pharm. Sci., Nov. 1974, pp. 1779–1783.

Higuchi, T., "Physical Chemical Analysis of Percutaneous Absorption Process from Creams and Ointments", J. soc. Cosmetic Chemists, pp. 85–93, Sep. 1959.

Chandrasekaran, S. K. et al., "Scopolomine Permation Through Human Skin in Vitro", AIChE J., Sep. 1976, pp. 828–832.

ESTRADIOL TRANSDERMAL DELIVERY SYSTEM

SCOPE OF THE INVENTION

The present invention is directed to a transdermal (or percutaneous) delivery system for estrogen and its derivatives. This delivery system is a drug-containing adhesive device which has a constant release rate over a period of time.

BACKGROUND OF THE INVENTION

Estradiol is the predominant estrogen secreted by the ovary during the reproductive era. The initial decline in ovarian function during perimenopause ultimately leads to an almost complete cessation of ovarian production of estrogens in the postmenopausal years. Thus, postmenopausal women are deficient principally in estradiol.

It is well recognized that in some women this deficiency rapidly results in the development of vasomotor symptoms and in atrophic changes within the genital tract. Additionally, certain psychological symptoms—such as anxiety, forgetfulness and difficulty in concentrating (i.e. "menopausal syndrome")—increase in frequency during the climactic and early postmenopausal years. Ovarian failure also has long-term consequences because postmenopausal women are at an increased risk of developing osteoporosis and certain fractures.

Replacement of estrogen during the climactic and postmenopausal period not only relieves all the acute symptoms but also appears to protect against both the development of osteoporosis and the occurrence of the fractures.

Currently, exogenous estrogen therapy is mainly prescribed by the oral route of administration: this therapy has certain disadvantages. High doses of estrogen must be administered because of the rapid metabolism and inactivation of estrogens by the gut wall and liver (first pass effect). It has been estimated that up to 30% of the administered dose is inactivated even before it reaches the systemic circulation.

The potential advantage of delivering estradiol transdermal is that gut wall and hepatic metabolism may be avoided, thus not only allowing the use of lower total daily doses but also diminishing the risks of hepatic enzyme induction and its sequelae. Transdermal delivery of estradiol can control menopausal symptoms effectively without inducting adverse metabolic changes.

U.S. Pat. No. 4,379,454 discloses a transdermal delivery system for estradiol. This system is a permeable membrane-controlled reservoir system that uses ethanol as a skin penetration enhancer. The estradiol is dissolved in the ethanol and both penetrate through the skin. A permeable membrane is used for containing the diffusion rate. An adhesive is applied on the permeable membrane. The stability of this system is short and the delivery rate is not constant. Moreover, the enhancer, ethanol, reacts with adhesive and causes lose of adhesion and, consequently, the system falls off the skin.

U.S. Pat. No. 4,390,520 discloses a transdermal delivery system for indomethacin. This system is a drug-containing adhesive device. The system comprises, in relevant part, indomethacin and a skin penetration enhancer, polyoxyethylene sorbitan mono-oleate ("polysorbate"), which are mixed into a adhesive copolymer, such as 2-ethylhexyl acrylate-vinyl acetate copolymer. The indomethacin is dissolved directly into the copolymer.

U.S. Pat. No. 4,420,470 discloses a transdermal delivery system for drugs useful in suppressing or preventing attacks of angina pectoris; the drugs are isosorbide dinitrate and pentaerythritol tetranitrate. This system is a drug-containing adhesive device. The system comprises, in relevant part, the drug and skin penetration enhancer, such as polyethylene glycol, mixed with an adhesive copolymer, such as 2-ethylhexyl acrylate-vinyl acetate copolymer.

U.S. Pat. Nos. 4,291,014; 4,321,252; and 4,438,139, which are deemed cumulative of one another, each disclose a transdermal delivery system for estrogen-type drugs. These systems are generally monolithic-type devices, i.e., an adhesive is interposed between the skin and matrix. For example, U.S. Pat. No. 4,438,139 discloses a matrix comprising a polar plasticizer, polyvinyl alcohol, polyvinyl pyrrolidone and estrogen. The polar plasticizer is polyethylene glycol and is necessary to make the matrix flexible and to increase the reliability of diffusional release of the estrogen. Additionally, a detergent (i.e. surfactant), such as sorbitan, and an absorption facilitator, may be added.

U.S. Pat. Nos. 4,058,122 and 4,077,407, which are deemed cumulative of one anther, each disclose a drug delivery system for estrogen. These systems are generally reservoir-type devices. For example, U.S. Pat. No. 4,058,122 discloses a system comprising a wall, having a passageway, which surrounds an active agent. In operation, the wall is permeable to external fluids which cross through the wall and which create an osmotic pressure within the wall. The osmotic pressure forces the drug from behind the wall and through the passageway. Materials which are added to the wall (lamina) to control flux through the wall include polyethylene glycol. Dispersants, which are added to the wall to produce an integral composite, include polyoxyethylenated sorbitan oleate having a to 20 moles of ethylene oxide.

SUMMARY OF THE INVENTION

The present invention is directed to a transdermal delivery system for an active substance. The active substance is estrogen or its derivatives and preferably is 17-beta-estradiol. The system comprises an impermeable backing layer and a matrix affixed thereto. The matrix comprises, on a weight percentage basis, from about 60 to about 95%. of an adhesive polymer, from about 5 to about 20% of a solvent, from about 0.2 to about 4% of a skin penetration enhancer, and from about 0.5 to about 5% of the active substance. The system is free of any discrete permeable, polymeric, diffusion-controlling membrane.

DESCRIPTION OF THE DRAWINGS

For the purpose of illustrating the invention, the drawings show a form in which is presently preferred; it being understood, however, that this invention is not limited to the precise arrangements and instrumentalities shown.

DETAILED DESCRIPTION OF THE INVENTION

Figure 1:
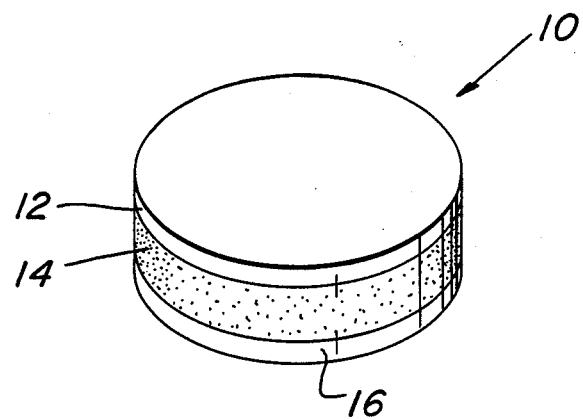
FIG. 1 is an isometric view of a preferred embodiment of the present invention.
Figure 2:
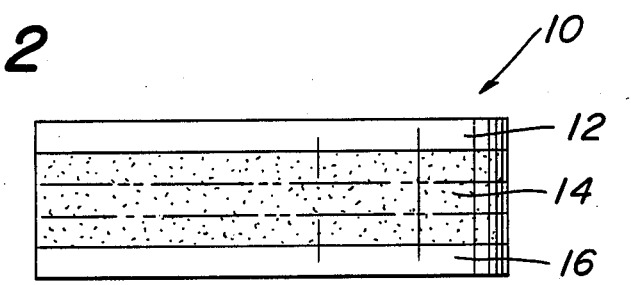
FIG. 2 is a sectional view taken generally along lines 2—2 in FIG. 1.

In the present invention, the transdermal delivery system 10 comprises an impermeable backing membrane 12, a polymeric diffusion matrix 14 which is preferably formed by one or more thin layers (illustrated in phantom) and is free of any discrete polymeric diffusion membrane. An example of such a diffusion membrane is set forth in U.S. Pat. No. 4,379,454 incorporated herein by reference. The impermeable backing membrane is well known in the art and is not limiting on the instant invention.

The matrix 14 is compounded on a weight percentage basis, from about 60 to about 95% of an adhesive polymer, from about 5 to about 20% of pharmaceutical grade solvent, from about 0.2 to about 4% of a skin penetration enhancer and from about 0.5 to about 5% of an active substance.

The adhesive polymer is a pressure sensitive adhesive and is acceptable for medical use. Of these types of polymer, either water base or solvent base materials may be used. These polymers have two functions in the instant invention. First, they are adhesive to the skin and securely hold the matrix on and in good diffusional contact with the skin. Second, they are the carrier or vehicle for storing the active substance. Preferably, the adhesive polymer is a vinyl acetate - acrylate multipolymer. Such a multipolymer is commercially available from the Monsanto Company, St. Louis, Mo., under the name of GELVA®. GELVA® 737, 788 and 2484 may be used. Specifically, GELVA® 737 comprises up to 1.1% of 2-ethylhexyl acrylate.

The active substance which is transdermally delivered to the systematic circulation of the body in therapeutically effective amounts is preferably 17-beta-estradiol. However, any estrogen or estrogen derivative, which are well known, may be used.

The solvent dissolves the active substance. The solvent is polyethylene glycol or polyethylene glycol esters or propylene glycol or combinations thereof. Polyethylene glycol, as used herein, means polyethylene glycol with average molecular weights of 200, 300, 400, 500 600 and 800 and its derivatives. Polyethylene glycol esters, as used herein, means polyethylene glycol monolaurate, polyethylene glycol mono-oleate and polyethylene glycol monopalmitate. The solvents described herein are commercially available from such companies as Emery Industries and BASF.

The skin penetration enhancer is a polyoxyethylene ethers, preferably polysorbate 80, i.e. sorbitan mono-9-octadecenoate poly (oxy-1,2-ethanediyl) and its derivatives. However, other polysorbates, such as polysorbate 21, 40, 60, 61, 65, 80, 81 and 85, may be used. Additionally, polyoxyethylene ethers of higher aliphatic alcohols, such as BRIJ® 52, 56, 58, 30, 35, 92, 96, 98, 72, 76, 78, 700, 721 and etc., may be used. BRIJ® is a trademark of ICI United States, Inc. of Delaware. Polysorbate 80 is a product of ICI, Wilmington, Del.

Figure 3:
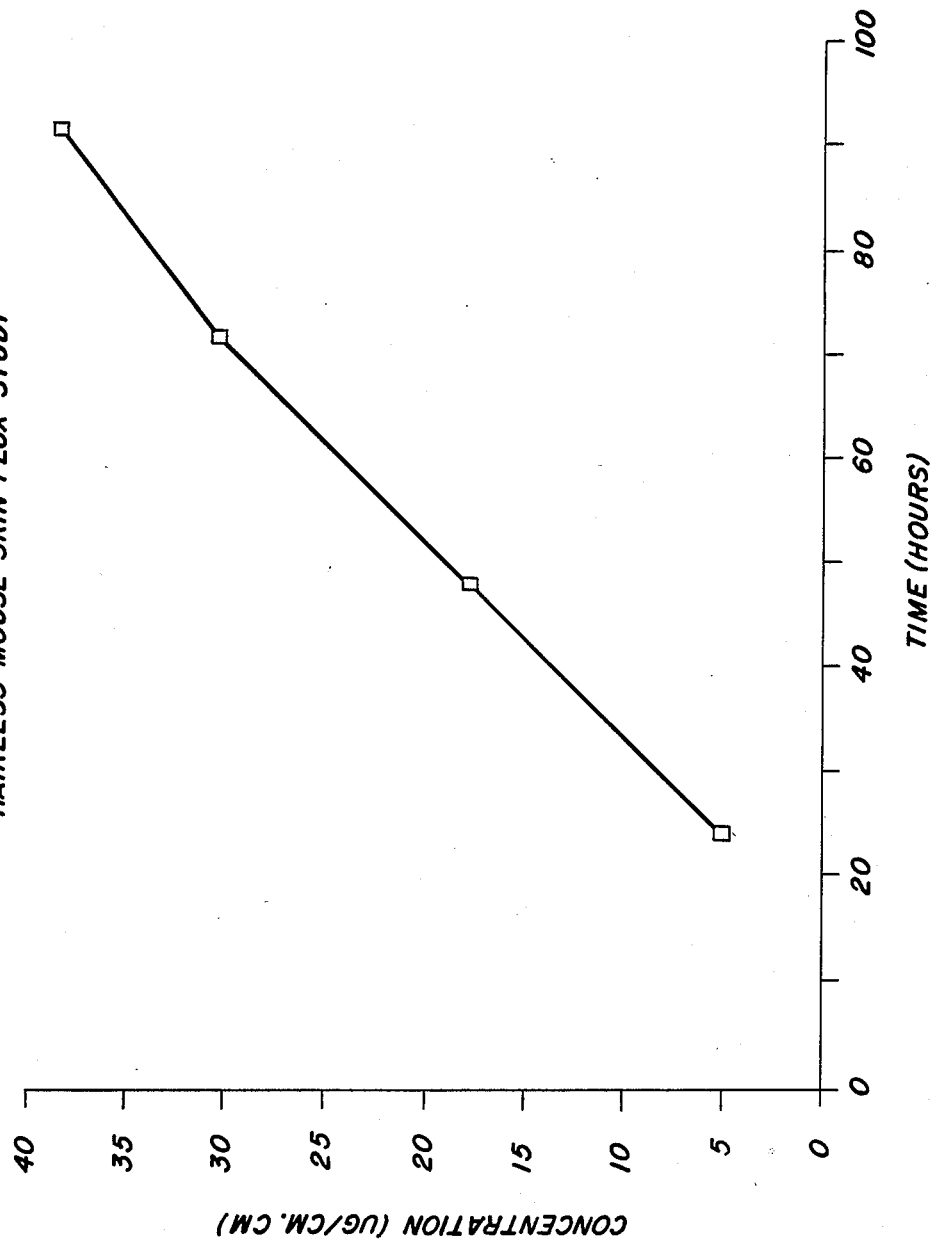
FIG. 3 is a graph illustrating the results of a hairless mouse skin flux study.
Figure 4:
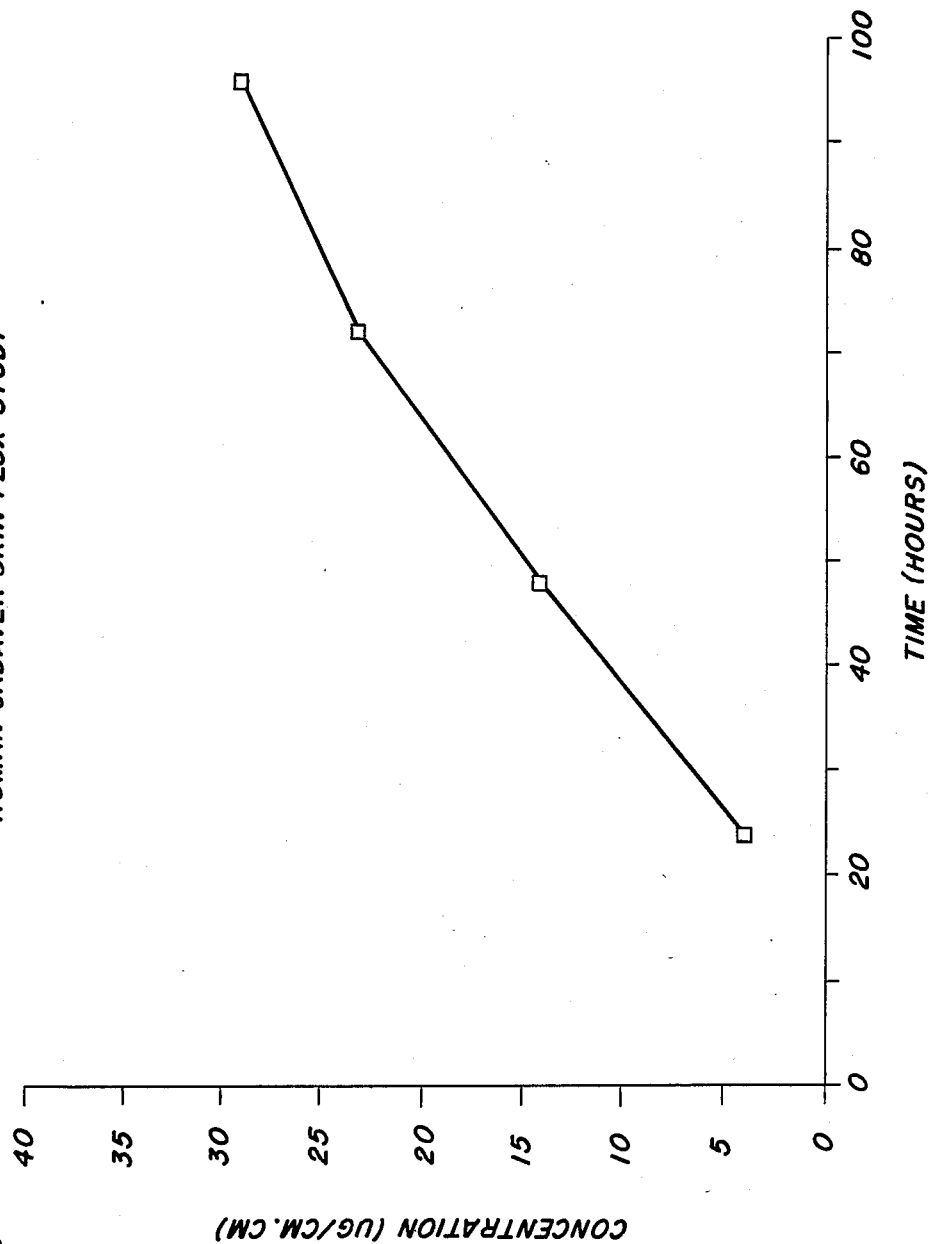
FIG. 4 is a graph illustrating the results of a human cadaver skin flux study.

In operation, the system is applied to the skin where the adhesive polymer affixes the system on the skin. The active substance, which is dissolved by the solvent, is disbursed throughout the matrix. The active substance diffuses from the matrix with the enhancer. At the stratum cornium, the enhancer facilitates the transdermal diffusion therethrough and into the systemic circulation. The transdermal flux of the active substance is substantially uniform. See FIGS. 3 and 4.

The preparation of the transdermal delivery system according to the present invention is accomplished as follows. The active substance is dissolved in the solvent and enhancer to form a solution. The solution is added to the polymer and mixed for about 20–30 minutes and then allowed to stand for about 20–60 minutes to eliminate the air bubbles. This mixture is cast on the impermeable membrane, a polyethylene film or aluminized polyethylene film made by 3M Company (e.g. 3M-Scotchpak 1006 or 3M-1012) and dried at about 40° C. to 50° C., for about 20–40 minutes. After drying the coating, a release liner 16, such as a silicon release paper or the like which are well known, is placed over the exposed surface of the matrix. Then the system is die cut into a optimum size. If multiple matrix layers are required, each subsequent layer is cast over or overlaps the previous layer. The finished system is put into a pouch and hermetically sealed.

EXAMPLE 1

To prepare the matrix, 0.2 g of 17 beta-estradiol is dissolved in 0.5 g of polyethylene glycol 200, 0.25 g of propylene glycol and 0.05 g of polysorbate 80, whereby a solution is formed. This solution is added to 10 g of polymer solution (Monsanto GELVA® 737) and then mixed for 20–30 minutes. After mixing, the mixture is settled for about 20 minutes to remove air bubbles and is cast onto the backing material (3M-Scotch Pak 1006 or 1012). The cast mixture is dried from 30 minutes at 45° C. To make a triple layers matrix, the 2nd and 3rd layers are sequentially cast over the prior layer after the prior layer is settled and dried. This formation is then cut into 4cm$^2$ shapes.

Hairless mouse skin flux study results for this matrix formulation are shown on Table 1.

EXAMPLE 2

0.1 g of 17 beta-estradiol is dissolved in 1.0 g of polyethylene glycol 400 and 0.01 g of polysorbate 60. This solution is mixed with 12 g of polymer solution (Monsanto GELVA® 788) for 25 minutes. After settling for 20 minutes, the mixture is cast onto the backing material. The remaining steps are the same as set forth in Example 1.

EXAMPLE 3

0.4 g of 17 beta-estradiol is dissolved in 6 g of polyethylene glycol 400, 2 g of propylene glycol and 0.5 g of diethylene glycol oleyl ether. This solution is mixed with 30 g of polymer solution (Monsanto GELVA® 2484) for 20 minutes. The remaining steps are set forth in Example 1.

EXAMPLE 4

0.5 g of 17 beta-estradiol is dissolved in 4 g of polyethylene glycol 400, 3 g of propylene glycol and 0.5 g of polysorbate 20. This solution is mixed with 20 g of polymer solution for 30 minutes. After settling for 20 minutes, the further steps set forth in Example 1 are followed.

The human cadaver skin flux study, results for this formulation are set forth in Table 2.

EXAMPLE 5

0.7 g of 17 beta-estradiol is dissolved in 15 g of polyethylene glycol 400, 0.5 g of polysorbate 60 and 3 g of propylene glycol. This solution is mixed with 25 g of polymer solution (Monsanto GELVA ® 737) for 25 minutes. The remaining steps are the same as set forth in Example 1.

EXAMPLE 6

0.3 g of 17 beta-estradiol is dissolved in 6 g of polyethylene glycol 400 monolaurate and 0.5 g of BRIJ ® 92. This solution is mixed with 30 g of polymer solution for 30 minutes. After settling for 20 minutes, the remaining steps are the same as set forth in Example 1.

The present invention may be embodied in other specific forms without departing from the spirit or essential attributes thereof and, accordingly, reference should be made to the appended claims, rather than to the foregoing specification, as indicating the scope of the invention.

TABLE 1

| Hairless Mouse Skin Flux Study (ug - micrograms) | | | |
|---|---|---|---|
| Time (hr) | Sample No. 1 | Sample No. 2 | Average |
| 24 | 5.913 ug | 4.323 ug | 5.118 ug |
| 48 | 15.565 ug | 9.563 ug | 12.609 ug |
| 72 | 14.207 ug | 10.985 ug | 12.596 ug |
| 92 | 8.904 ug | 7.358 ug | 8.131 ug |

TABLE 2

| Human Cadaver Skin Flux Study (ug - micrograms) | | | |
|---|---|---|---|
| Time (hr) | Sample No. 1 | Sample No. 2 | Average |
| 24 | 5.276 ug | 2.554 ug | 3.915 ug |
| 48 | 12.432 ug | 7.737 ug | 10.085 ug |
| 72 | 13.006 ug | 5.376 ug | 9.191 ug |
| 96 | 5.053 ug | 6.206 ug | 6.030 ug |

I claim:

1. A transdermal delivery system comprises:
an impermeable backing layer;
a matrix affixed to said backing layer and comprising on a weight percentage basis from about 60 to about 95% of an adhesive vinyl acetate-acrylate multipolymer, from about 5 to about 20% of a solvent, from about 0.2 to about 4% of a skin penetration enhancer, and from about 0.5 to about 5% of an active substance selected from the group consisting of estrogen, derivatives of estrogen and combinations thereof; and
said system being free of any discrete, permeable, polymeric, diffusion-controlling membrane.

2. The system according to claim 1 wherein said active substance is 17-beta-estradiol.

3. The system according to claim 1 wherein said solvent is selected from the group consisting of propylene glycol, propylene glycol derivatives and combinations thereof.

4. The system according to claim 1 wherein said solvent is selected from the group consisting of polyethylene glycol having approximate molecular weights of 200, 300, 400, 500, 600 and 800, and polyethylene glycol ester such as polyethylene glycol monolaurate, monooleate, and monolaurate, and combinations thereof.

5. The system according to claim 1 wherein said skin penetration enhancer is a polyoxyethylene ester.

6. The system according to claim 1 wherein said skin penetration enhancer is sorbitan mono-9-octadecenoate poly(oxy-1,2-ethanediyl) and its derivatives.

7. The system according to claim 1 further comprising a release layer, whereby said matrix is sandwiched between said backing layer and said release layer prior to use.

8. A transdermal delivery system comprises:
an impermeable backing layer;
a matrix affixed to said backing layer and comprising on a weight percentage basis from about 60 to about 95% of an adhesive vinyl acetate-acrylate multipolymer, from about 5 to about 20% of a solvent selected from the group consisting of propylene glycol, propylene glycol derivatives and combinations thereof, from about 0.2 to about 4% of a polyoxyethylene ester skin penetration enhancer, and from about 0.5 to about 5% of an active substance selected from the group consisting of estrogen, derivatives of estrogen and combinations thereof; and
said system being free of any discrete, permeable, polymeric, diffusion-controlling membrane.

* * * * *